United States Patent
Wong et al.

(10) Patent No.: US 12,408,980 B2
(45) Date of Patent: Sep. 9, 2025

(54) COOLED CHOKES FOR ABLATION SYSTEMS AND METHODS OF USE

(71) Applicant: INTUITIVE SURGICAL OPERATIONS, INC., Sunnyvale, CA (US)

(72) Inventors: Serena H. Wong, Los Altos, CA (US); Joseph D. Bogusky, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/343,550

(22) Filed: Jun. 28, 2023

(65) Prior Publication Data
US 2023/0338086 A1    Oct. 26, 2023

Related U.S. Application Data

(63) Continuation of application No. 16/681,255, filed on Nov. 12, 2019, now Pat. No. 11,730,537.
(Continued)

(51) Int. Cl.
*A61B 18/18* (2006.01)
*A61B 18/00* (2006.01)

(52) U.S. Cl.
CPC ..... *A61B 18/18* (2013.01); *A61B 2018/00011* (2013.01); *A61B 2018/00577* (2013.01); *A61B 2018/183* (2013.01)

(58) Field of Classification Search
CPC .......... A61B 2018/00011; A61B 2018/00577; A61B 2018/183; A61B 2018/00023; A61B 2018/00029; A61B 18/18; A61B 18/1815; A61B 18/08; A61B 18/149; A61B 18/183; A61B 2090/374; A61B 2090/376; A61B 2090/378; A61B 2090/3925; A61B 34/20; A61B 34/25; A61B 34/30; A61B 34/35; A61B 34/74; A61B 2218/002; A61B 2034/2051; A61B 2034/2065; A61B 2034/254; A61B 2034/258;
(Continued)

(56) References Cited

U.S. PATENT DOCUMENTS

| 4,823,812 A | 4/1989 | Eshel et al. |
| 6,380,732 B1 | 4/2002 | Gilboa |

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Joanne M Rodden
*Assistant Examiner* — Abigail M Ziegler
(74) *Attorney, Agent, or Firm* — Haynes & Boone, LLP

(57) ABSTRACT

An antenna system for tissue ablation comprises an energy transmission member, an antenna body coupled to the energy transmission member, a fluid source, and a choke member including a choke body and a choke connector electrically coupling the choke body to the energy transmission member. The choke connector is in direct contact with fluid from the fluid source and forms a delivery path for the fluid between the choke body and the energy transmission member. The choke connector and the choke body are integrally formed of a continuous wire mesh.

13 Claims, 13 Drawing Sheets

Related U.S. Application Data

(60) Provisional application No. 62/760,583, filed on Nov. 13, 2018.

(58) Field of Classification Search
CPC ........ A61B 2034/2061; A61B 17/3478; A61B 2017/00955; A61B 2018/00791; A61B 2018/00809; A61B 2018/00875; A61B 2018/00982; A61B 2018/1876; A61B 2018/00077; A61B 2018/00595; A61B 2018/00738; A61B 2018/00916; A61B 2018/0094; A61B 2018/1853; A61B 2018/1861; A61B 2018/1892; A61B 2018/00202; A61B 2018/00571; A61B 2018/1823
See application file for complete search history.

(56) References Cited

U.S. PATENT DOCUMENTS

| | | |
|---|---|---|
| 6,389,187 B1 | 5/2002 | Greenaway et al. |
| 7,416,681 B2 | 8/2008 | Kim et al. |
| 7,772,541 B2 | 8/2010 | Froggatt et al. |
| 8,280,525 B2 | 10/2012 | Rusin et al. |
| 8,292,881 B2 | 10/2012 | Brannan et al. |
| 8,876,814 B2 | 11/2014 | Bonn |
| 8,900,131 B2 | 12/2014 | Chopra et al. |
| 9,192,437 B2 | 11/2015 | Brannan et al. |
| 9,247,992 B2 | 2/2016 | Ladtkow et al. |
| 9,259,274 B2 | 2/2016 | Prisco |
| 9,452,276 B2 | 9/2016 | Duindam et al. |
| 11,730,537 B2 | 8/2023 | Wong et al. |
| 2006/0013523 A1 | 1/2006 | Childlers et al. |
| 2010/0305559 A1* | 12/2010 | Brannan ............ A61B 18/1815 606/33 |
| 2011/0077635 A1* | 3/2011 | Bonn .................. H01Q 9/16 343/906 |
| 2014/0000098 A1 | 1/2014 | Dunning et al. |
| 2014/0046316 A1 | 2/2014 | Ladtkow et al. |
| 2014/0296839 A1 | 10/2014 | Brannan |
| 2015/0038956 A1 | 2/2015 | Amabile et al. |
| 2016/0058507 A1 | 3/2016 | Dickhans |
| 2017/0231696 A1 | 8/2017 | Williams et al. |
| 2018/0036069 A1 | 2/2018 | Dickhans et al. |
| 2018/0036070 A1 | 2/2018 | Dickhans et al. |
| 2020/0188021 A1 | 6/2020 | Wong et al. |

\* cited by examiner

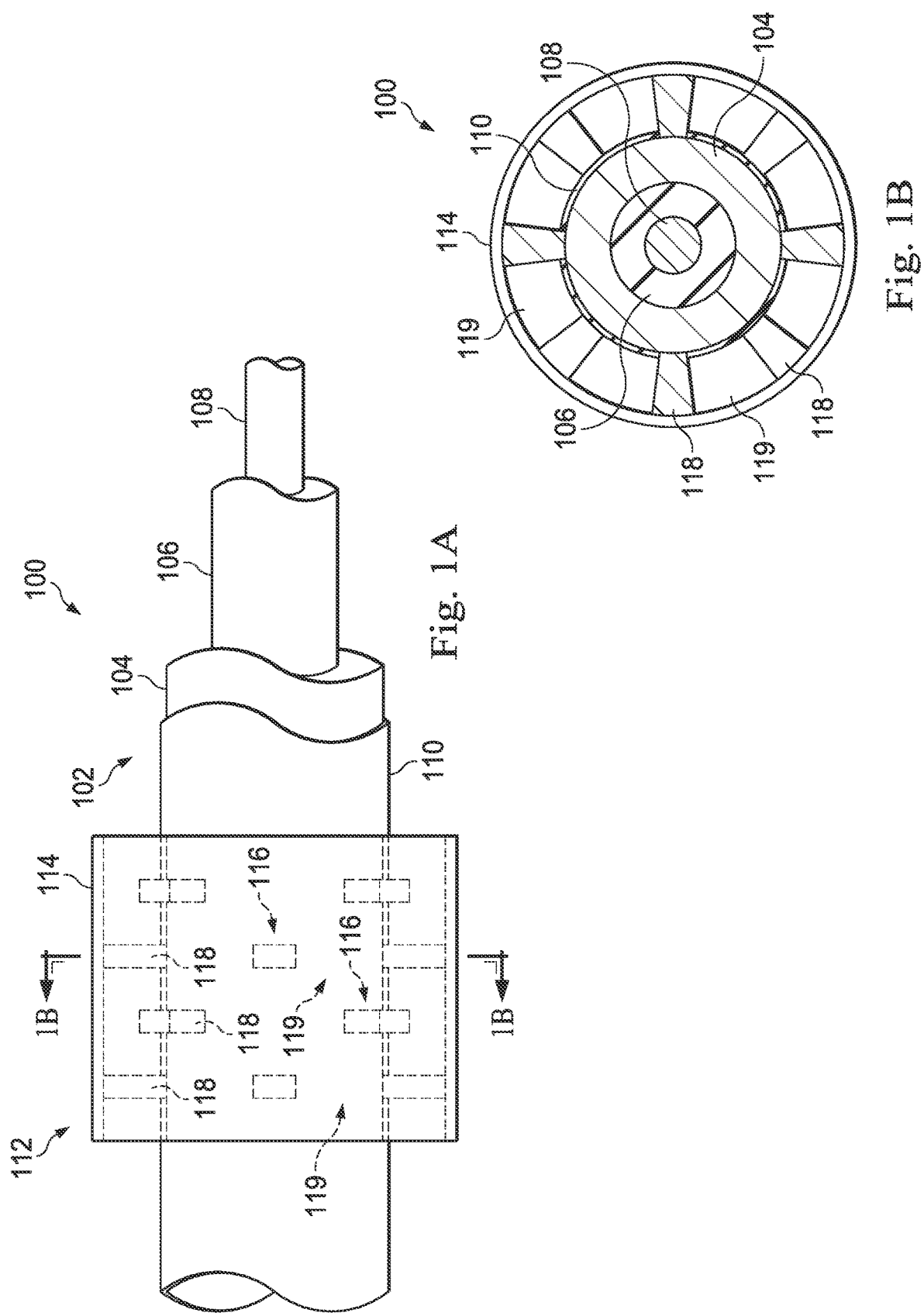

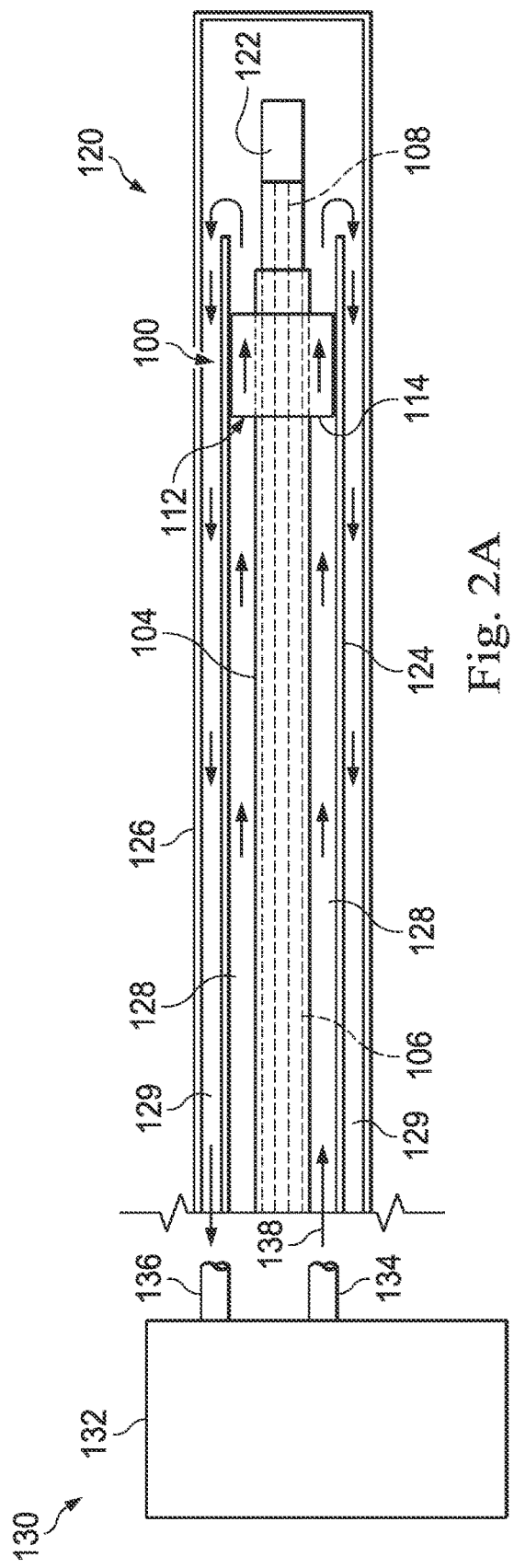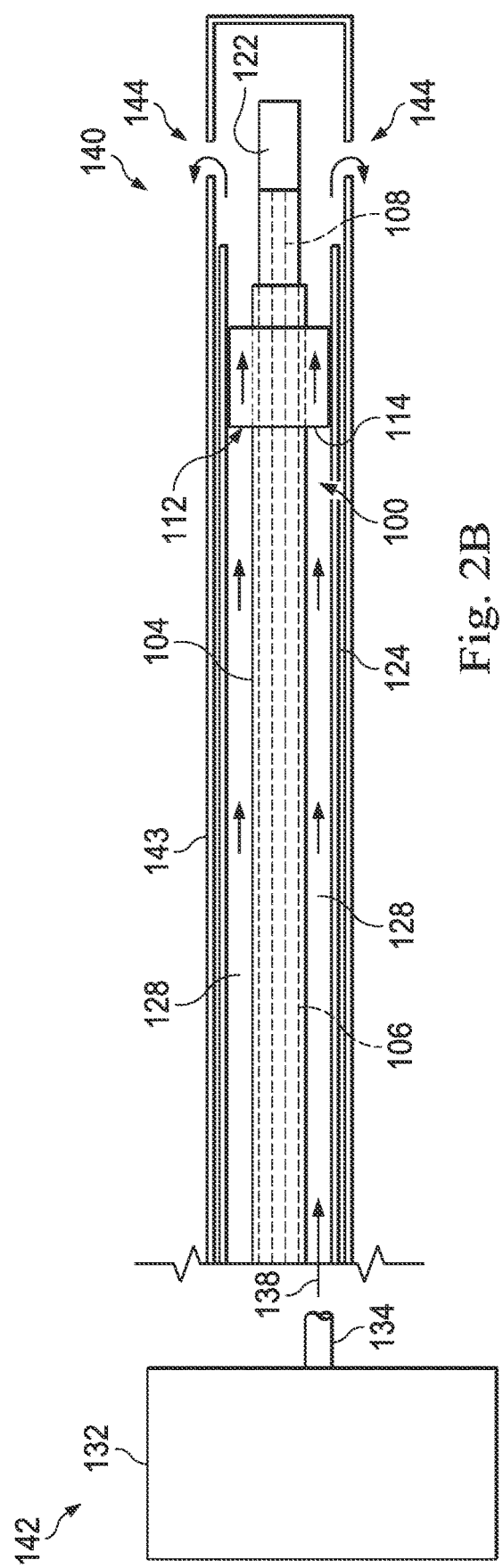

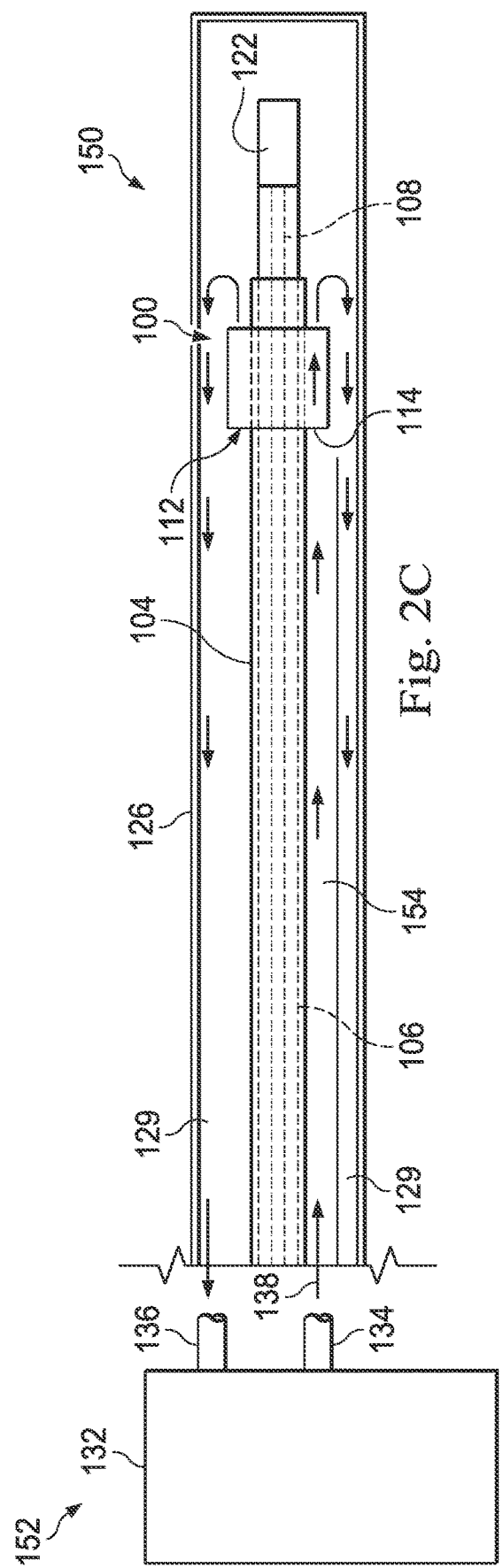

COOLED CHOKES FOR ABLATION SYSTEMS AND METHODS OF USE

CROSS-REFERENCE TO RELATED APPLICATIONS

This application is the continuation of U.S. patent application Ser. No. 16/681,255 filed Nov. 12, 2019, which claims the benefit of U.S. Provisional Application No. 62/760,583, filed Nov. 13, 2018, both of which are incorporated by reference herein in their entirety.

FIELD

The present disclosure is directed to minimally invasive ablation systems and methods of use and more particularly to systems and methods for cooling minimally invasive ablation systems and associated chokes.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Minimally invasive medical tools may also include ablation instruments. Ablation instruments transmit energy in the form of electromagnetic waves to a targeted area of tissue, such as a tumor or other growth, within the patient anatomy to destroy the targeted tissue. Some minimally invasive medical tools and ablation instruments may be teleoperated or otherwise computer-assisted. Various features may improve the effectiveness of minimally invasive ablation instruments.

SUMMARY

Embodiments of the invention are best summarized by the claims that follow the description.

Consistent with some embodiments, an antenna system for tissue ablation may comprise an energy transmission member, an antenna body coupled to the energy transmission member, a fluid source, and a choke member including a choke body and a choke connector electrically coupling the choke body to the energy transmission member. The choke connector may be in direct contact with fluid from the fluid source and forms a delivery path for the fluid between the choke body and the energy transmission member. The choke connector and the choke body may be integrally formed of a continuous wire mesh.

Consistent with some embodiments, a method for delivering ablation energy may comprise conducting energy through an energy transmission member and conducting energy through a choke member coupled to the energy transmission member. The choke member includes a choke body and a choke connector electrically coupling the choke body to the energy transmission member. The choke member may be formed from a continuous wire mesh. The method may further comprise providing fluid from a cooling system through the choke member such that the choke connector is in direct contact with the fluid.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 1A illustrates a partial view of an antenna assembly with a choke member according to some embodiments.

FIG. 1B illustrates a cross-sectional view of the antenna assembly of FIG. 1A according to some embodiments.

FIG. 2A illustrates a schematic view of fluid flow in an antenna system according to some embodiments.

FIG. 2B illustrates a schematic view of fluid flow in an antenna system according to some embodiments.

FIG. 2C illustrates a schematic view of fluid flow in an antenna system according to some embodiments.

Figure 3:
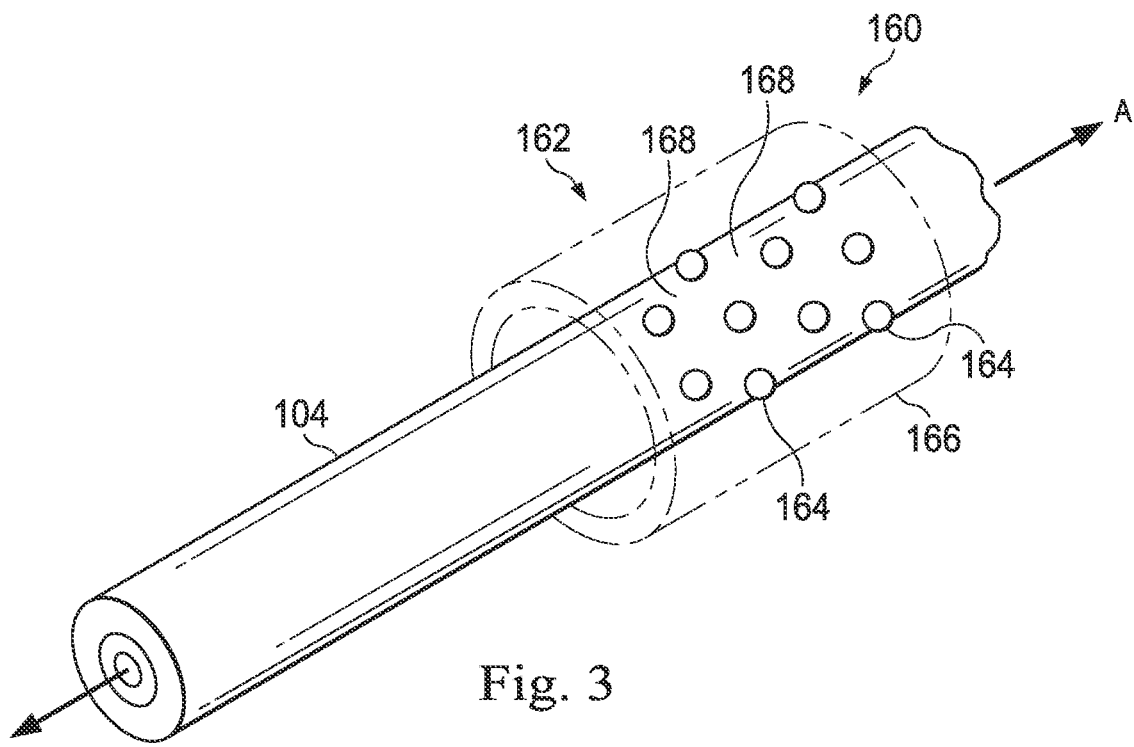
FIGS. 3-9 illustrate partial views of antenna systems with choke members according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Various embodiments of antenna systems with choke members are described herein. In some embodiments, the antenna systems are used for tissue ablation, causing an increase in a temperature of an anatomic target area by transmitting electromagnetic waves from the antenna system to the anatomic target area, or ablation site. In some embodiments, antenna systems may be flexible and suitable for use in, for example, surgical, diagnostic, therapeutic, ablative, and/or biopsy procedures. In some embodiments, antenna systems may include choke members to control current flow and localized power application. In some embodiments, the antenna systems may be used as a medical instrument in an image-guided medical procedure performed with a teleoperated medical system as described in further detail below. While some embodiments are provided herein with respect to such procedures, any reference to medical or surgical instruments and medical or surgical methods is non-limiting. In some embodiments, the antenna systems may be used for non-teleoperational procedures involving traditional manually operated medical instruments. The systems, instruments, and methods described herein may be used for animals, human cadavers, animal cadavers, portions of human or animal anatomy, non-surgical diagnosis, as well as for industrial systems and general robotic, general teleoperational, or robotic medical systems.

As shown in FIGS. 1A and 1B, an antenna assembly 100 generally includes an elongate energy transmission member 102. The elongate energy transmission member 102 includes an outer conductor 104 substantially surrounding a dielectric layer 106 and an inner conductor 108. An insulating jacket 110 may extend over the outer conductor 104. In this embodiment, elongate energy transmission member 102 is a coaxial cable. Other coaxial cable configurations with different configurations, shapes, etc. of inner conductor, outer conductor, and dielectric layers could also be used. In alternative embodiments, other configurations of elongate energy transmission members may be used. The antenna assembly 100 also includes a choke member 112 including a choke body 114 extending around and concentric with a portion of the elongate transmission member 102. The choke body 114 may be formed from a tubular section of metal, a tubular mesh structure, a helical metal structure, or other types of conductive structures concentric with the energy transmission member. The choke member 112 also includes a choke connector 116 with connector components 118 electrically coupling the choke body 114 to the outer conductor 104, through the jacket 110. A network of passages 119 extend through spaces between the connector components 118. In addition to providing a uniform current flow to the choke body 114, the spaced apart connector components 118 provide flexibility to the antenna assembly 100. The choke member 112 may be used to control current path and electromagnetic wave pattern generated by the antenna assembly 100. More specifically, the choke member may function to cancel currents flowing on the outside of the outer conductor 104 which may lead to excess heating of the antenna assembly. As will be described in greater detail, the network of passages 119 create a fluid delivery path, allowing a cooling fluid to pass through the choke member 112 to control the heat generated by the antenna assembly 100.

As shown in FIG. 2A, the antenna assembly 100 may be part of an antenna system 120. In this embodiment, an antenna body 122 is coupled to the antenna assembly 100. More specifically, the antenna body 122 may be electrically coupled (e.g., soldered) to the inner conductor 108 or the outer conductor 104. The antenna body 122 may be used to radiate microwave energy for use in the tissue ablation process. More specifically, antenna body 122 is used to create electromagnetic radiation within a wavelength range of one meter to one millimeter, and within a frequency range of approximately 300 Megahertz (MHz) to 300 Gigahertz (GHz) (e.g., a microwave). A microwave, which is a type of radio wave, is made up of a magnetic field at a right angle to an electric field, and both the magnetic field and the electric field oscillate at a specific frequency and travel together along a direction that is perpendicular to both the magnetic field and the electric field. The microwave radiation from the combined antenna assembly 100 and antenna body 122 maybe modified and controlled by the choke member 112 to cause a desired type of ablation at an ablation target site.

Antenna assembly 100 may be disposed within a flexible tubular member 124 that extends over the energy transmission member 102, the choke member 112, and optionally over the antenna body 122, forming a delivery passage 128. The tubular member 124 is open at a distal end near the antenna body 122. Antenna body 122, antenna assembly 100, and tubular member 124 are disposed within a sheath 126. In this embodiment the sheath 126 is closed, sealed, or otherwise restricts fluid from passing outside of the sheath. A return path or passage 129 extends between the tubular member 124 and the sheath 126.

The antenna system 120 also includes a fluid cooling system 130 in fluid communication with the antenna assembly 100. Fluid cooling system 130 includes a fluid source 132 containing a cooling fluid which may be a liquid or a gaseous material. The cooling fluid may be chosen, based on its dielectric constant, to efficiently operate the antenna system. For example, water or other high dielectric constant fluids may be used to reduce a length dimension of the antenna system. Fluid cooling system 130 also includes a supply conduit 134 coupled between fluid source 132 and delivery passage 128 and a return conduit 136 coupled in fluid communication between fluid source 132 and the return passage 129. Fluid cooling system 130 may also include pumps, valves, reservoirs or other components not shown in detail. Some or all of the components of the fluid cooling system 130 may be located outside a patient anatomy when the antenna system 120 is used for tissue ablation. The supply conduit 134 supplies a flow 138 of the fluid from fluid source 132 to the passage 128 to control the temperature along antenna assembly 100 and antenna body 122, thereby minimizing the risk of overheating patient tissue at the target site and/or reducing distortion of a heating zone during the ablation process. For example, the fluid cooling system may be used to prevent charring of target tissue due to an over-temperature situation of the target tissue at the target site. An over-temperature situation may result from conductive and/or radiative heating of elements of antenna system 120 and/or the target tissue during operation of antenna system 120.

In this embodiment, fluid cooling system 130 is a closed loop system. Supply conduit 134 may be coupled in fluid communication with the passage 128 such that cooling fluid is supplied along the energy transmission member 102 and through the choke member 112. The fluid is discharged within sheath 126 after exiting the tubular member 124. The discharged fluid may then be caused to flow through the return passage 129 to return conduit 136. The fluid flow may be generated, for example, by a pressure differential between supply conduit 134 and return conduit 136.

FIG. 2B illustrates an antenna system 140 with an open loop fluid cooling system. Some components of the system 140 are the same or substantially similar to previously described components and are identified with the same numerical identifier. In this embodiment, a fluid cooling system 142 is an open-loop fluid cooling system. Fluid cooling system 142 supplies cooling fluid through supply conduit 134 to delivery passage 128 and finally through one or more outlet ports 144 extending through a sheath 143. Outlet ports 144 are positioned to discharge the cooling fluid from sheath 143 into the patient anatomy or into a catheter device in which the antenna system 140 may be extended. In some embodiments, the cooling fluid discharged through outlet ports 144 may be used to flush and/or cool the ablation target site. Fluid cooling system 142 may be utilized, for example, in the open-loop configuration where bathing an ablation site in the cooling fluid is beneficial to the ablation process. In this embodiment the outlet ports are near a distal end of sheath 143, but in alternative embodiments, outlet ports may be located at any position along the surface of the sheath, including through a distal end.

FIG. 2C illustrates an antenna system 150 with a closed loop fluid cooling system. Some components of the system 150 are the same or substantially similar to previously described components and are identified with the same numerical identifiers. In this embodiment, a fluid cooling system 152 is a closed-loop fluid cooling system. Fluid cooling system 152 supplies cooling fluid through supply conduit 134 to a delivery tube 154 that extends parallel to the outer conductor 104 within the sheath 126. In this embodiment, the delivery tube 154 terminates near the proximal end of the choke member 112. Fluid flows through the delivery tube 154, dispenses through the choke member 112, and is returned to the fluid source 132 via the return passage 129. The fluid flow may be generated, for example, by a pressure differential between supply conduit 134 and return conduit 136.

FIG. 3 illustrates a partial view of an antenna assembly 160 with a choke member 162 concentric with outer conductor 104. The antenna assembly 160 may be used within a fluid-cooled assembly system (e.g., system 120, 140, 150). The choke member 162 includes a choke body 166 electrically coupled to the outer conductor 104 by a choke connector comprising a plurality of conductive beads 164. The conductive beads may be spherical, hemispherical, or any other raised shape. In one example, the conductive beads may be solder bumps or dots. The conductive beads 164 may be arranged in rows perpendicular to a longitudinal axis A of the energy transmission member 102, columns parallel to the longitudinal axis A, spirals around the axis A, or other patterns around the circumference of the outer conductor 104. Spaces 168 extend between the beads 164 forming a delivery path allowing cooling fluid from a fluid cooling system to flow into direct contact with the beads and between the choke body 166 and the outer conductor 104. The arrangement of the beads 164 may minimize blockage of the flow of electrical current, keeping the current flow to the choke body 166 generally uniform.

Figure 4:
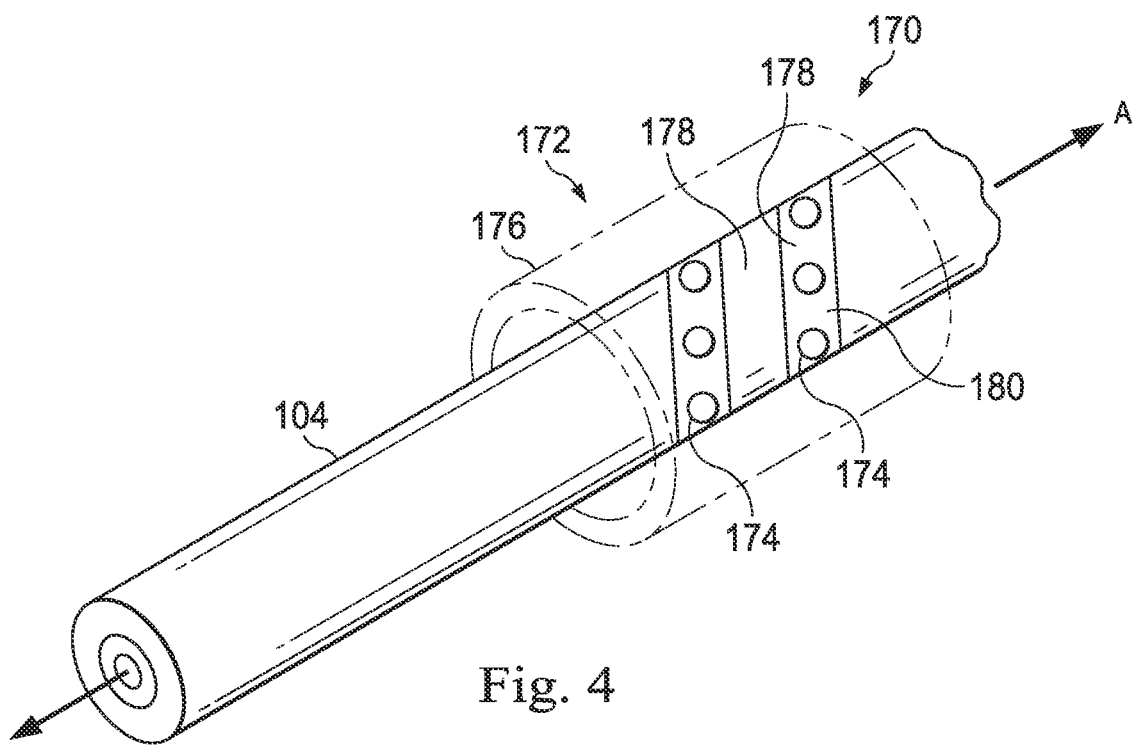

FIG. 4 illustrates a partial view of an antenna assembly 170 with a choke member 172 concentric with outer conductor 104. The antenna assembly 170 may be used within a fluid-cooled assembly system (e.g., system 120, 140, 150). The choke member 172 includes a choke body 176 electrically coupled to the outer conductor 104 by a choke connector comprising a plurality of conductive beads 174. The conductive beads 174 may be fixed to a flexible medium 180 such as a sheet, strip, film, or other matrix that allows the conductive beads to be prearranged before flexible medium 180 is attached to the outer conductor 104. In one example, the flexible medium may be a polymer strip that allows conductive beads 174 to be wrapped around the outer conductor 104 in a helical pattern. The conductive beads may be spherical, hemispherical, or any other raised shape. In one example, the conductive beads may be solder bumps or dots. Spaces 178 extend between the beads 174 forming a delivery path allowing cooling fluid from a fluid cooling system to flow into direct contact with the beads and between the choke body 176 and the outer conductor 104. The arrangement of the beads 174 may minimize blockage of the flow of electrical current, keeping the current flow to the choke body 176 generally uniform.

Figure 5:
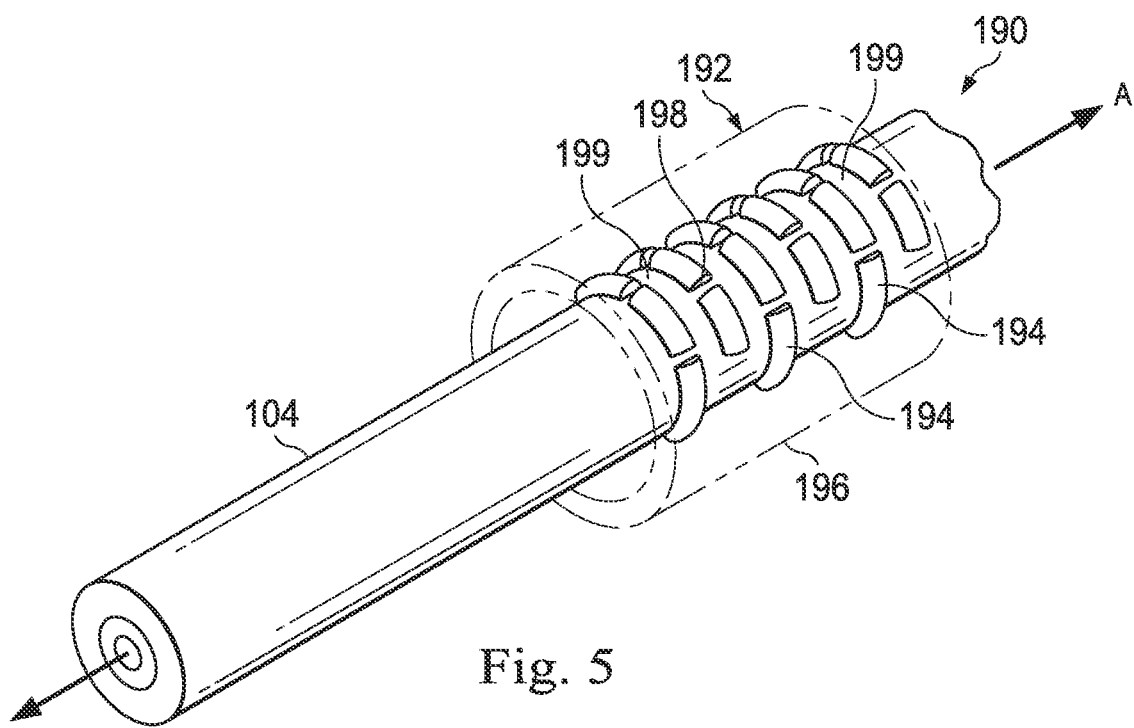

FIG. 5 illustrates a partial view of an antenna assembly 190 with a choke member 192 concentric with outer conductor 104. The antenna assembly 190 may be used within a fluid-cooled assembly system (e.g., system 120, 140, 150). The choke member 192 includes a choke body 196 electrically coupled to the outer conductor 104 by a choke connector comprising a plurality of raised curved projections 194. The curved projections 194 may be arranged in rows perpendicular to a longitudinal axis A of the energy transmission member 102 or in other patterns around the circumference of the outer conductor 104. The curved projections 194 may be generally arcuate in shape and curved around the axis A. In other embodiments, the curved projections may have an undulating shape with a plurality of curves around the axis A. Each of the curved projections 194 may extend less than 360 degrees around the outer conductor 104. The ends 198 of the curved projections 194 may be parallel to the axis A or may be skewed or curved relative to the axis A. Spaces 199 extend between the curved projections 194 forming a delivery path allowing cooling fluid from a fluid cooling system to flow into direct contact with the curved projections and between the choke body 196 and the outer conductor 104. The arrangement of the curved projections 194 may minimize blockage of the flow of electrical current, keeping the current flow to the choke body 196 generally uniform.

Figure 6:
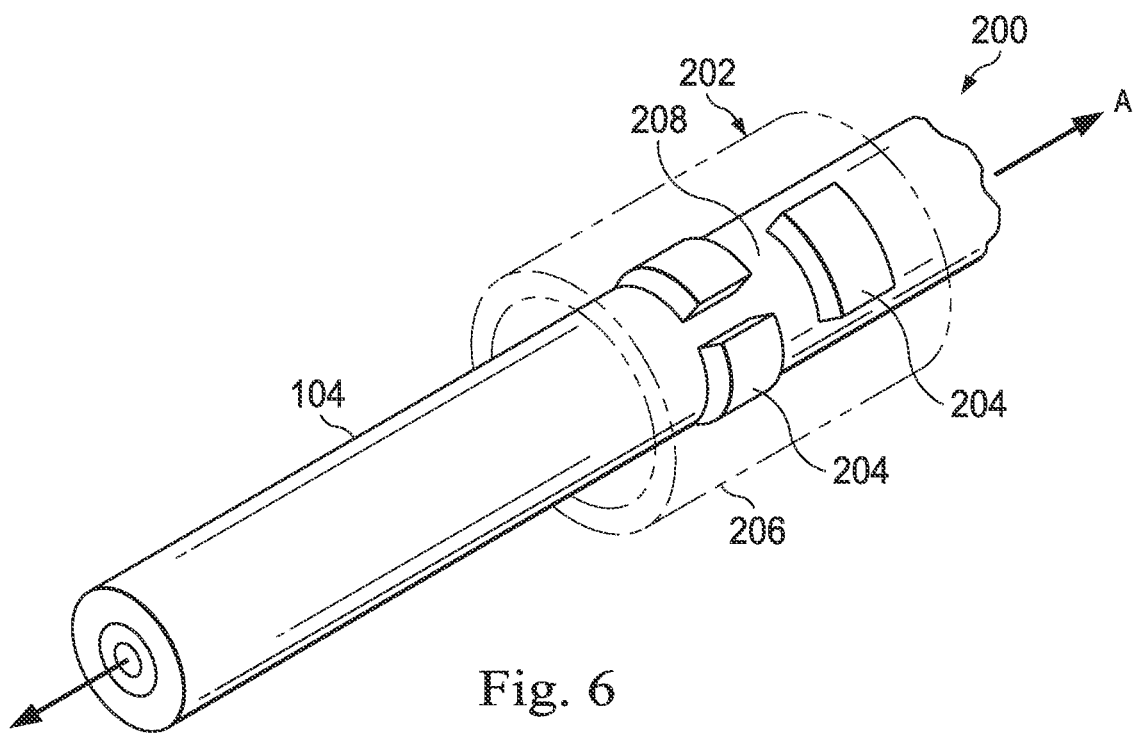

FIG. 6 illustrates a partial view of an antenna assembly 200 with a choke member 202 concentric with outer conductor 104. The antenna assembly 200 may be used within a fluid-cooled assembly system (e.g., system 120, 140, 150), The choke member 202 includes a choke body 206 electrically coupled to the outer conductor 104 by a choke connector comprising a plurality of raised curved projections 204. The curved projections 204 may be arranged in a spiral pattern or in a multi-row spiral pattern around the longitudinal axis A of the energy transmission member 102. Each of the curved projections 204 may extend less than 360 degrees around the outer conductor 104. Spaces 208 extend between the curved projections 204 forming a delivery path allowing cooling fluid from a fluid cooling system to flow into direct contact with the curved projections and between the choke body 206 and the outer conductor 104. The arrangement of the curved projections 204 may minimize blockage of the flow of electrical current, keeping the current flow to the choke body 206 generally uniform.

Figure 7:
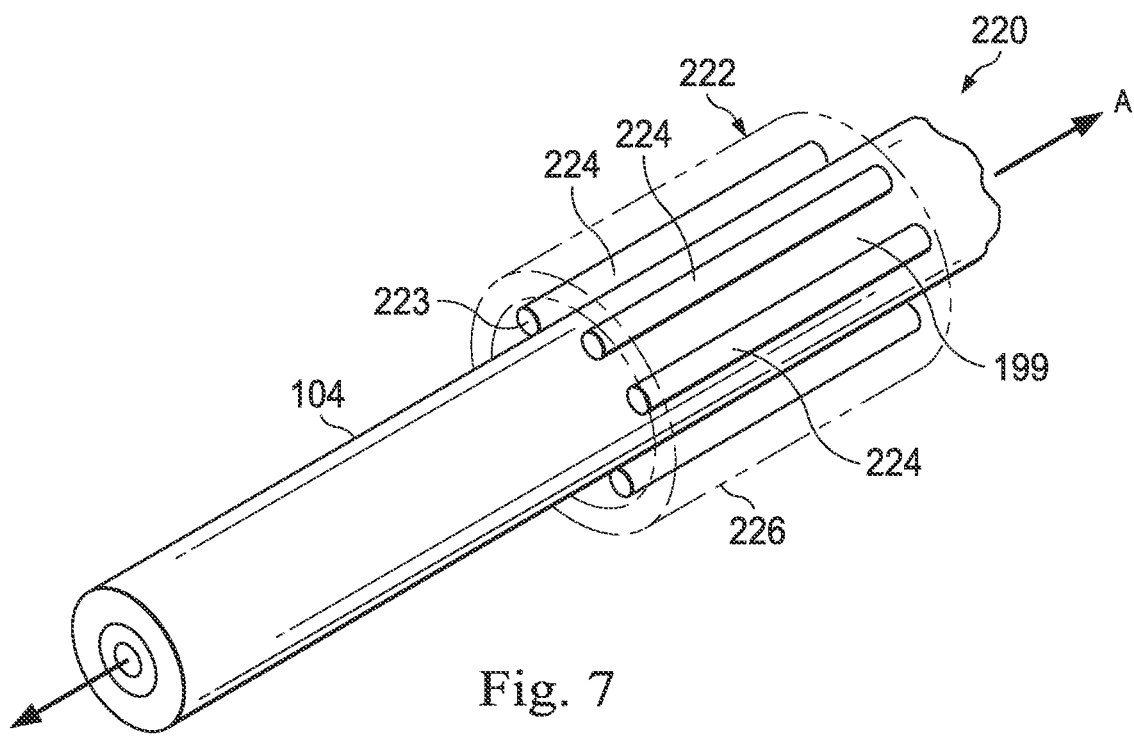

FIG. 7 illustrates a partial view of an antenna assembly 220 with a choke member 222 concentric with outer conductor 104. The antenna assembly 220 may be used within a fluid-cooled assembly system (e.g., system 120, 140, 150). The choke member 222 includes a choke body 226 electrically coupled to the outer conductor 104 by a choke connector comprising a plurality of electrically conductive tubes 224. The tubes 224 may be arranged in a concentric pattern parallel to the axis A or, in alternative embodiments, may be wrapped around the outer conductor 104 in a spiral pattern. Cooling fluid from the fluid cooling system may flow into direct contact with the tubes 224, either through fluid delivery paths formed by lumens 223 of the tubes 224 and/or through the spaces 199 between the tubes 224 and between the choke body 206 and the outer conductor 104. The tubes 224 may minimize blockage of the flow of electrical current, keeping the current flow to the choke body 206 generally uniform. In various embodiments, solid rods may replace the tubes 224 with cooling fluid flowing in the spaces 199 around the rods.

Figure 8:
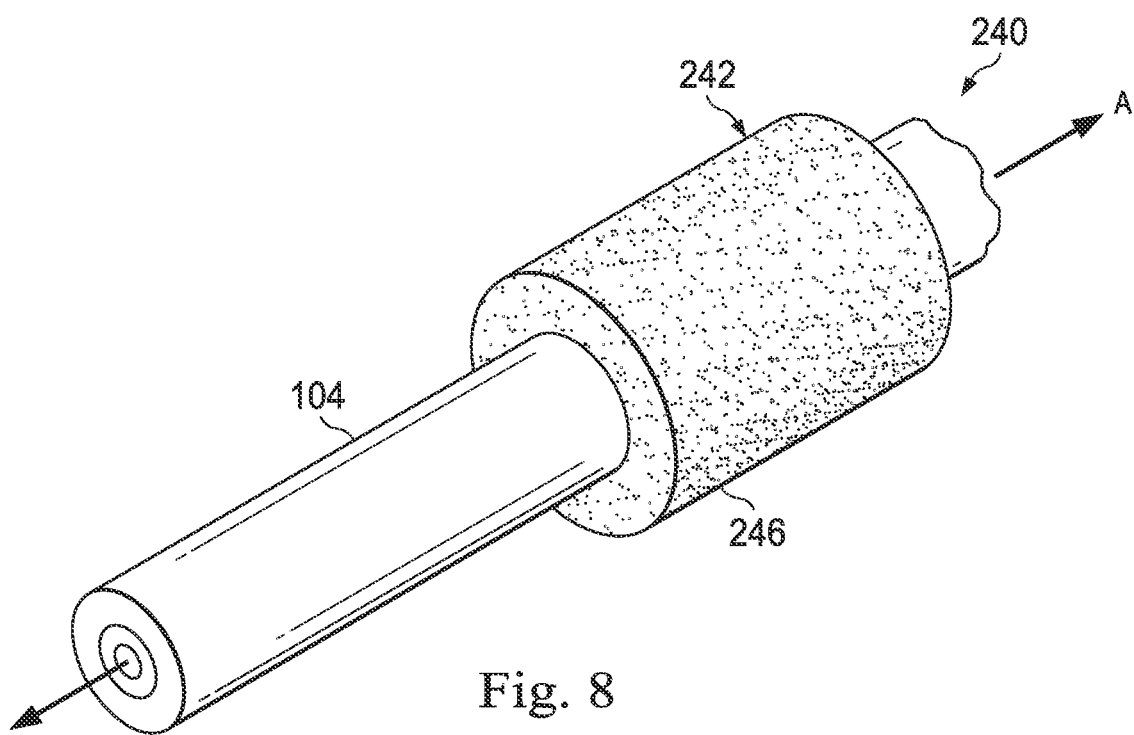

FIG. 8 illustrates a partial view of an antenna assembly 240 with a choke member 242 concentric with outer conductor 104. The antenna assembly 240 may be used within a fluid-cooled assembly system (e.g., system 120, 140, 150). The choke member 242 includes a choke body 246 electrically coupled to the outer conductor 104. In this embodiment, the choke member 242 may be formed from an open cell metal foam material that provides electrical conductivity from the outer conductor 104 through the sponge-like choke member 242. The open cell choke member 242 may be generally tubular in shape and concentric with axis A. The choke member 242 may extend between the outer conductor 104 and the sheath 126. Cooling fluid from the fluid cooling system may flow through the pores of the open cell choke member 242 which form fluid delivery paths through the choke member 242. The open cell conductive material may provide more flexibility than a solid metal member.

Figure 9:
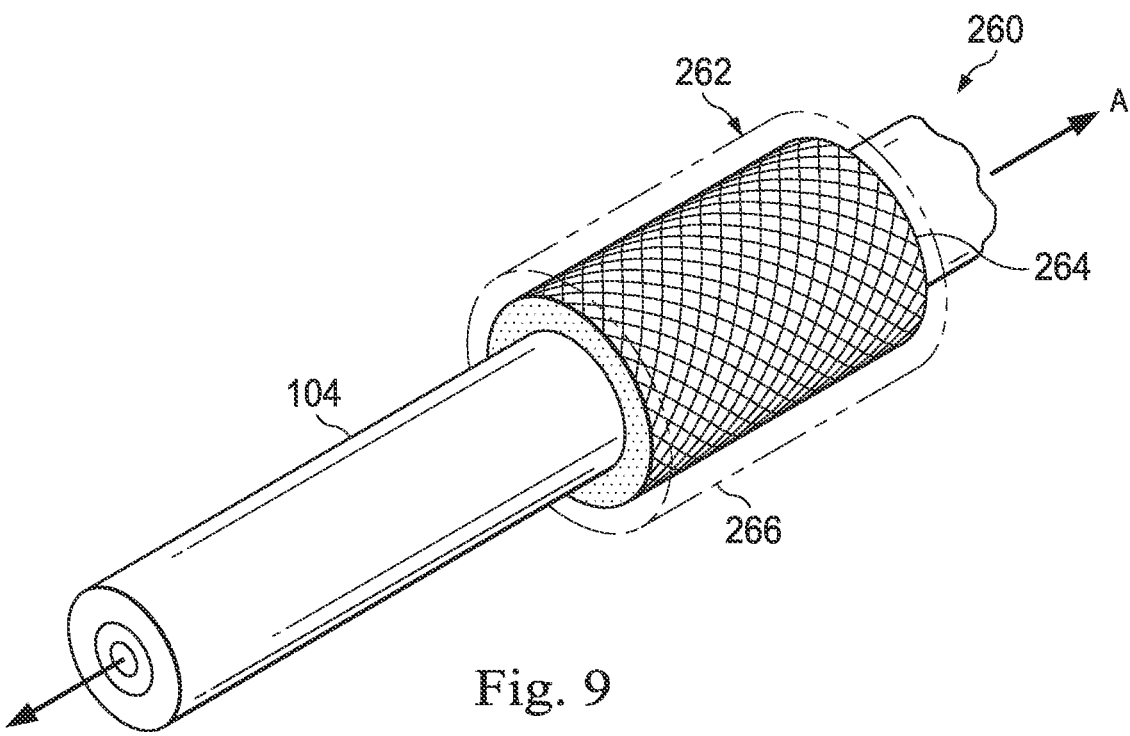

FIG. 9 illustrates a partial view of an antenna assembly 260 with a choke member 262 concentric with outer conductor 104. The antenna assembly 260 may be used within a fluid-cooled assembly system (e.g., system 120, 140, 150). The choke member 262 includes a choke body 266 electrically coupled to the outer conductor 104 by a choke connector comprising a conductive mesh member 264. The choke body 266 may be formed from a tubular section of metal, a tubular mesh structure, a helical metal structure, or other types of conductive structures concentric with the energy transmission member, as previously described. The conductive mesh member 264 may be arranged concentrically around axis A, between the choke body 266 and the outer conductor 104. The mesh forms fluid delivery paths such that cooling fluid from the fluid cooling system may flow through the openings in the mesh member 264 between the choke body 206 and the outer conductor 104. The mesh member 264 may have perforated openings that are shaped as squares or any other suitable shape. In some embodiments, the mesh member may be braided wire or other conductive strands. The mesh member 264 may minimize blockage of the flow of electrical current, keeping the current flow to the choke body 266 generally uniform.

Figure 10:
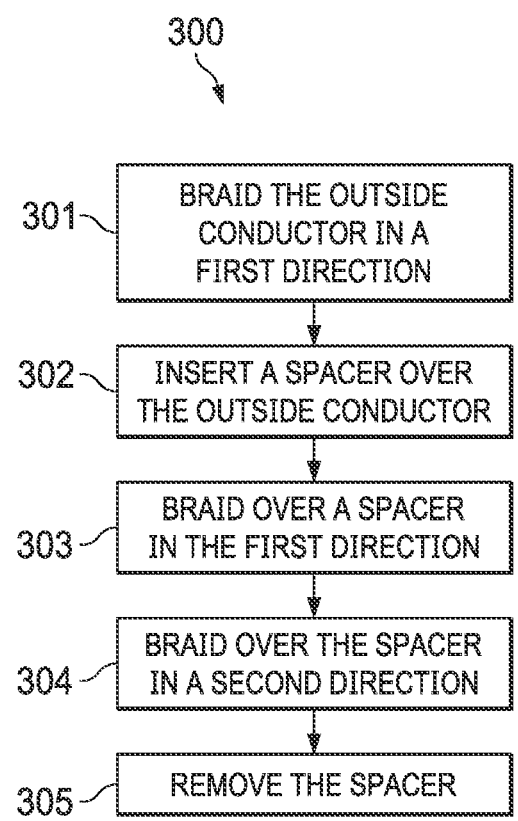
FIG. 10 illustrates a method for forming an antenna choke member according to some embodiments.

FIG. 10 illustrates a method 300 for forming an antenna choke member according to some embodiments. The method 300 is illustrated as a set of operations or processes. Not all of the illustrated processes may be performed in all embodiments of method 300. Additionally, one or more processes that are not expressly illustrated in FIG. 10 may be included before, after, in between, or as part of the processes. In some embodiments, one or more of the processes may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes may be performed by a control system (e.g., control system 412).

Figure 11A:
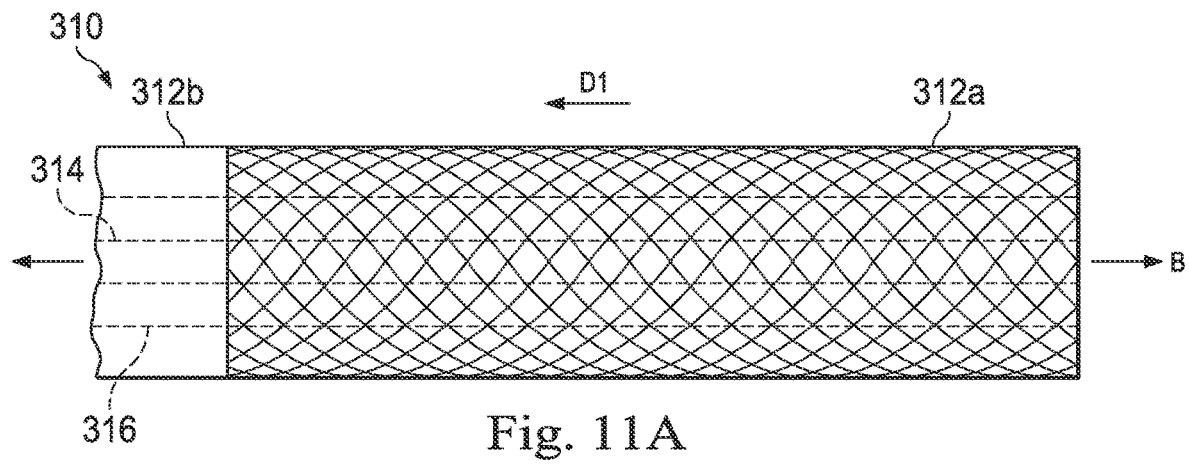
FIGS. 11A-11D illustrates a sequence of views of a procedure for forming a choke member according to some embodiments.

At a process 301 and with reference to FIG. 11A, an outer conductor is formed by braiding a braided outer conductor layer 312a over an outer conductor layer 312b. The outer conductor formed of layers 312a/312b are formed over an inner conductor 314 and a dielectric layer 316 to form an energy transmission member 310. The braiding may be performed by a braiding machine using conductive metallic strands to form a mesh braid. The braiding machine may rotate and translate while applying wires to form the mesh. In one example, the braiding may initially progress in a direction D1 along the longitudinal axis B to form the outer conductor layer in a single layer. In another example, the outer conductor layer can be formed of multiple layers of wire mesh by altering the direction of the braiding.

Figure 11B:
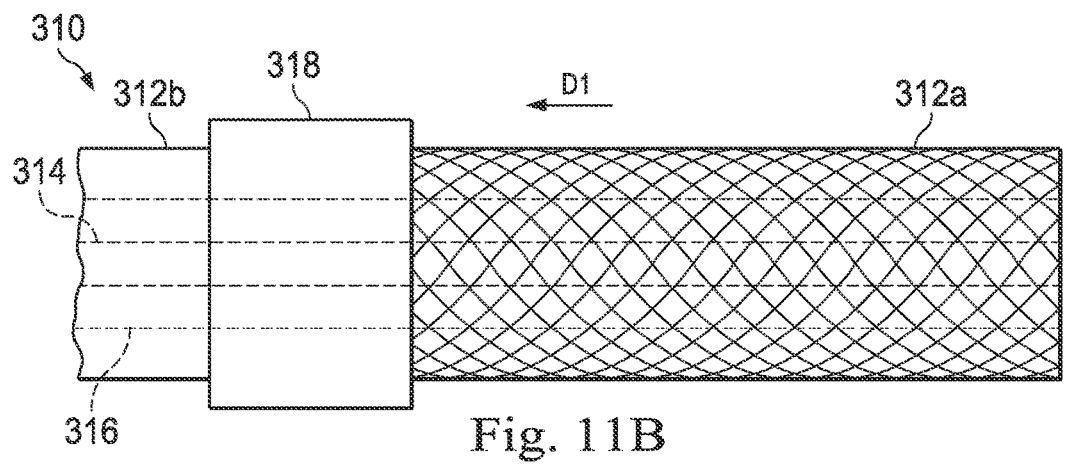
Figure 11C:
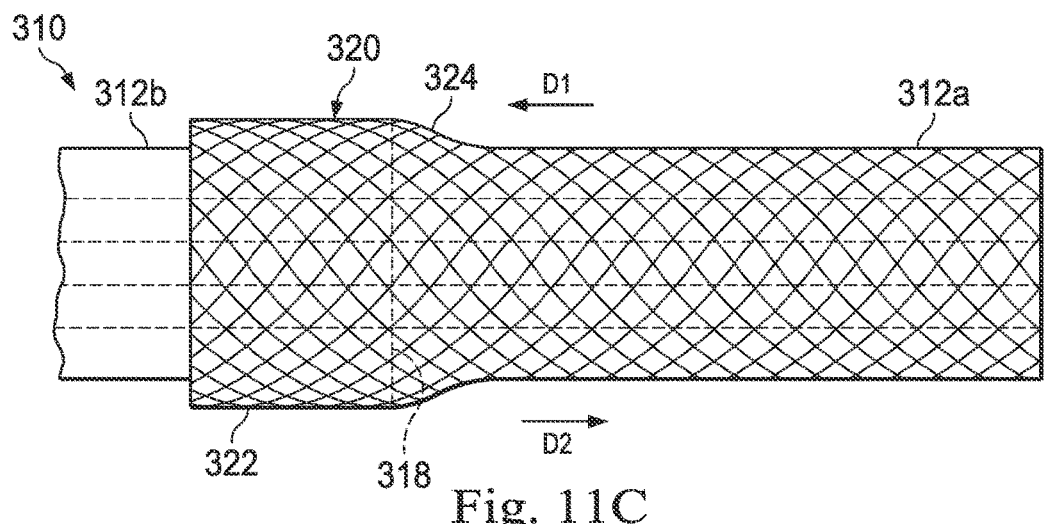

At a process 302, a spacer 318 may be inserted over the braided outer conductor layer 312a to serve as a form for creating a choke member 320 as shown in FIG. 11B. At a process 303, the spacer 318 is braided over in the direction D1 to form a choke member 320 as shown in FIG. 11C. At a process 304, the spacer 318 is braided over in the direction D2. Thus, a two layer braid formed over the spacer 318. Alternatively, more layers may be achieved by continuing the braiding in alternating directions. At a process 305, the spacer 318 may be removed having created a choke member 320 including a choke body 322 and a choke connector 324 coupling the choke body and the outer conductor layer 312a. With the spacer 318 removed, the choke body 322 is spaced apart from the outer conductor 312a/312b by a gap such that the choke body forms a cup-shaped structure around a distal portion of the outer conductor 312a/312b. Optionally, the entire braided structure may be laminated with a lamination material such as Teflon or may be overlayed with a jacket such as a Teflon jacket.

Figure 11D:
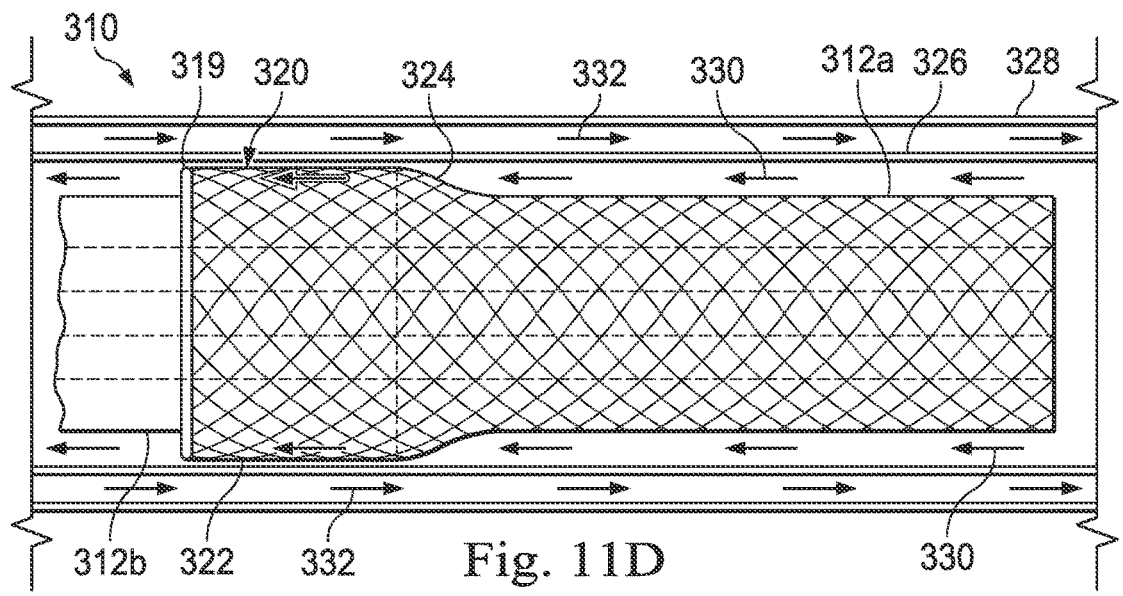

As shown in FIG. 11D, a tubular member 326 may be formed along the energy transmission member 310 and over the choke member 320. The tubular member 326 may be substantially similar to tubular member 124. The tubular member 326 may extend with a sheath 328 which may be substantially similar to sheath 126. Cooling fluid from the fluid cooling system (e.g., systems 130, 142, 152) may flow 330 within the tubular member 326 through the braided choke connector 324 and choke body 322. A return flow 332 of the cooling fluid is returned through the return passage between the tubular member 326 and the sheath 328. Because the choke member 320 is created from braid, the choke member 320 allows for passage of fluid flow through the choke member 320 and in contact with the choke member 320. The braided choke member 320 is formed from the same braid forming the outer conductor layer 312a so provides for electrical coupling between the outer conductor layer 312a and the choke body 322, while also being uniformly created during the braiding process which may minimize blockage of the flow of electrical current, keeping the current flow to the choke body 322 generally uniform.

As described, the outer conductor layer 312a and the choke member 320 may be formed of a continuous braided material. In alternative embodiments, the outer conductor may be braided separately from the mesh choke member 320 and the two may be connected (e.g., soldered) together. In alternative embodiments, the spacer may be omitted in the formation of the choke member and instead an end of the outer conductor mesh may be teased or fanned out to form the choke member. In alternative embodiments, the braided choke member may optionally be sealed at a distal end with a sealant 319. In this sealed choke embodiment, the sheath may extend to the proximal end of the choke so that cooling fluid flows in through the tubular member 326, dispenses into the sealed choke member and returns through the return passage between the tubular member 326 and the sheath 328. In alternative embodiments, the first braid layer may be formed separately (i.e. not continuously) from the second braid layer and the two layers may be welded together.

Figure 12:
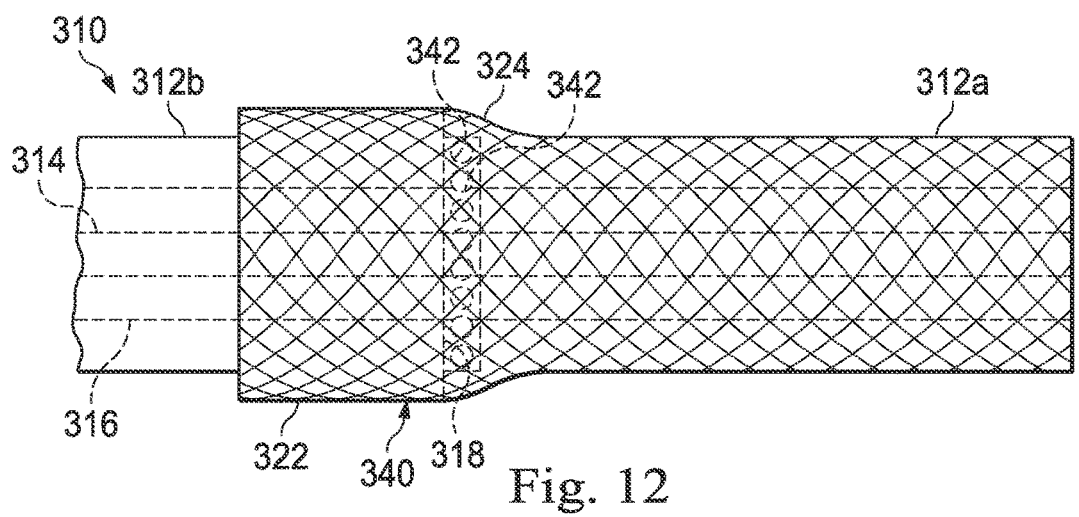
FIGS. 12-15 illustrate a partial views of antenna systems with a choke member according to some embodiments.

FIG. 12 illustrates an alternative choke member 340 used with energy transmission member 310. In this embodiment, after the braided outer conductor is formed (process 301) and before the spacer is inserted over the outer conductor (process 302), a set of pins 342 are wrapped around and connected to the outer conductor layer 312a. The pins 342 will pierce any jacket or protective coating extending over the outer conductor layer 312a. In some embodiments the pins 342 may be initially coupled to a flexible strip that is wrapped around the outer conductor. After the pins are connected to the outer conductor layer 312a, the flexible strip may be removed from the set of pins 342 allowing the pins to remain coupled to the outer conductor. After the pins 342 are in place, the method 300 may continue by inserting the spacer adjacent to the pins, and the spacer and pins may be braided over in multiple directions. The pins 342 form part of the choke connector such that cooling fluid from the fluid cooling system may flow between the pins and through the braided mesh choke connector 324 between the choke body 322 and the outer conductor layer 312a.

Figure 13:
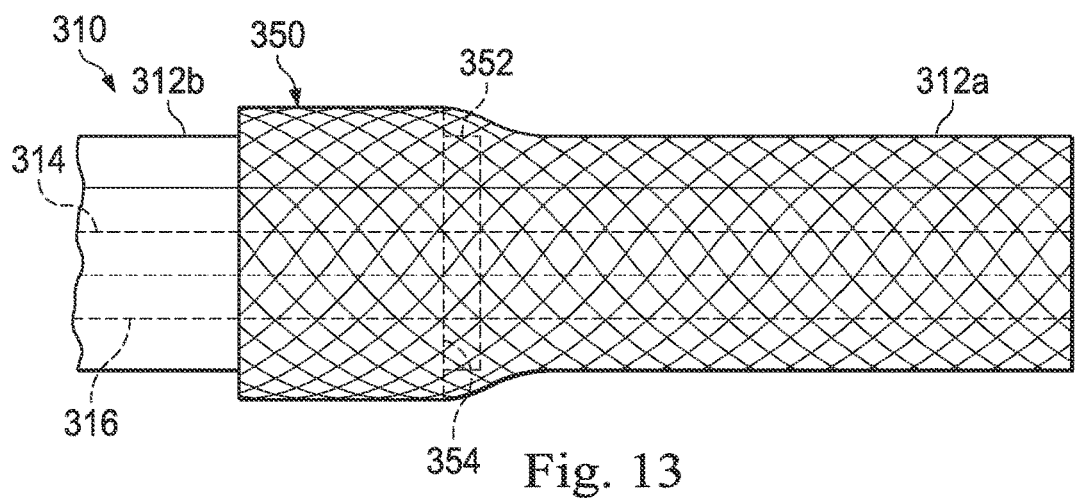

FIG. 13 illustrates an alternative choke member 350 used with energy transmission member 310. In this embodiment, after the braided outer conductor layer 312a is formed (process 301) a band is etched into the outer conductor and a conductive ring member 352 is placed in the etched band, thus electrically coupling the ring member 352 to the outer conductor layer 312a as a choke connector. A portion of a hypotube 354 may form a choke body and may be placed around the energy transmission member 310, adjacent to the ring member 352. The hypotube 354 and the ring member 352 may be braided over to form the choke member 350.

Figure 14:
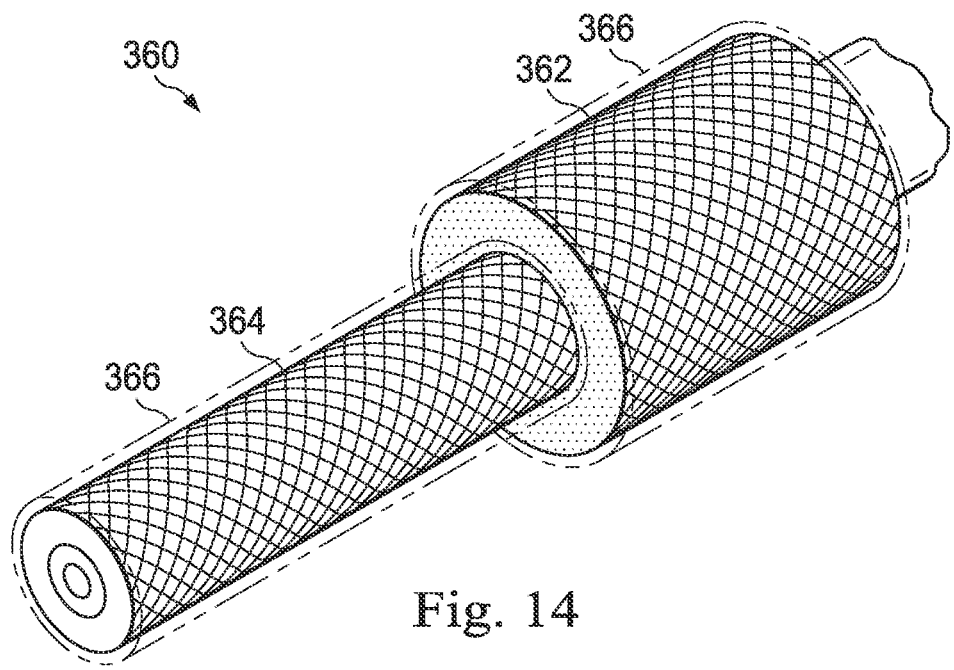

FIG. 14 illustrates a partial view of an antenna assembly 360 with a choke member 362 concentric with an outer conductor 364. The outer conductor 364 and the choke member 362 may be formed of a braided mesh material. In this embodiment, a sealant layer 366 may be applied to the braided mesh material to minimize the ingress of fluid that may degrade antenna performance. The sealant layer 366 may be painted, sputtered, evaporated, deposited, or otherwise applied to the braided mesh.

Figure 15:
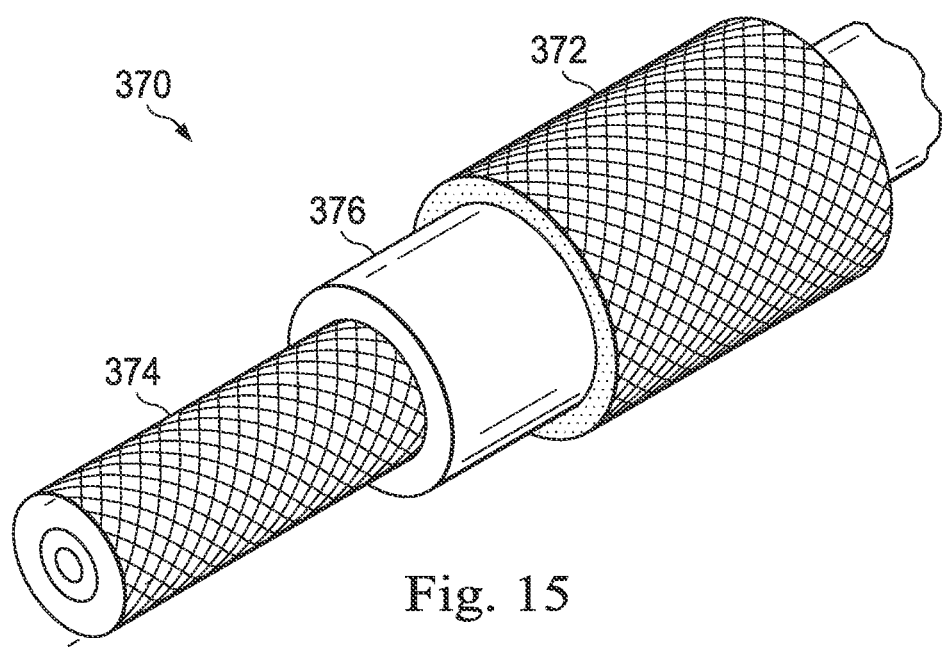

FIG. 15 illustrates a partial view of an antenna assembly 370 with a choke member 372 concentric with an outer conductor 374. The outer conductor 374 and the choke member 372 may be formed of a braided mesh material. In this embodiment, a sealed cap 376 is clamped around the outer conductor 374 to limit water ingress that may degrade antenna performance.

Figure 16:
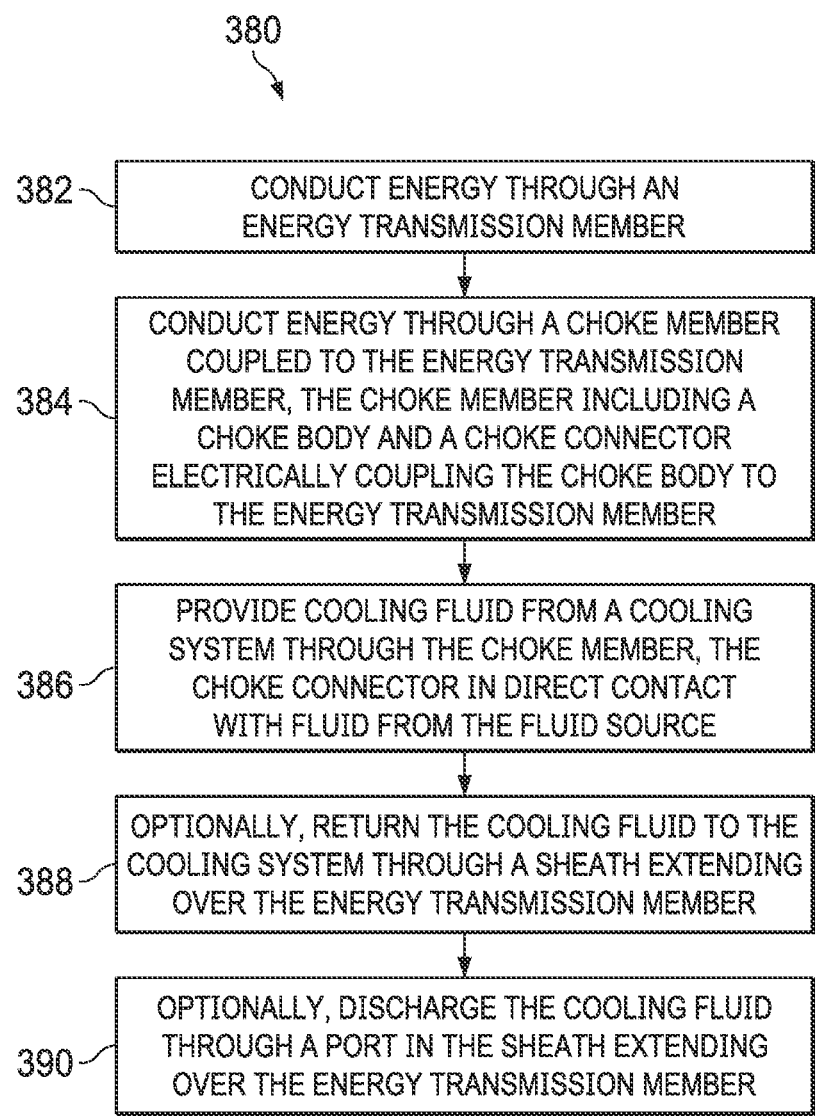
FIG. 16 illustrates a method for transferring energy to an ablation site according to some embodiments.

FIG. 16 illustrates a method 380 for transferring energy to an ablation site according to some embodiments. The method 380 is illustrated as a set of operations or processes. Not all of the illustrated processes may be performed in all embodiments of method 380. Additionally, one or more processes that are not expressly illustrated in FIG. 16 may be included before, after, in between, or as part of the processes. In some embodiments, one or more of the processes may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes may be performed by a control system (e.g., control system 412).

At a process 382, energy is conducted through an energy transmission member (e.g. energy transmission member 102). At a process 384, energy is conducted through a choke member (e.g., choke member 112) coupled to the energy transmission member. As described in the preceding embodiments, the choke member may include a choke body and a choke connector electrically coupling the choke body to the energy transmission member. At a process 386, cooling fluid is provided from a cooling system through the choke member. The fluid may directly contact the choke connector. At an optional process 388, the cooling fluid is returned to the cooling system through a sheath extending over the energy transmission member. Alternatively, at an optional process 390, the cooling fluid may be discharged through a port in the sheath extending over the energy transmission member.

Figure 17:
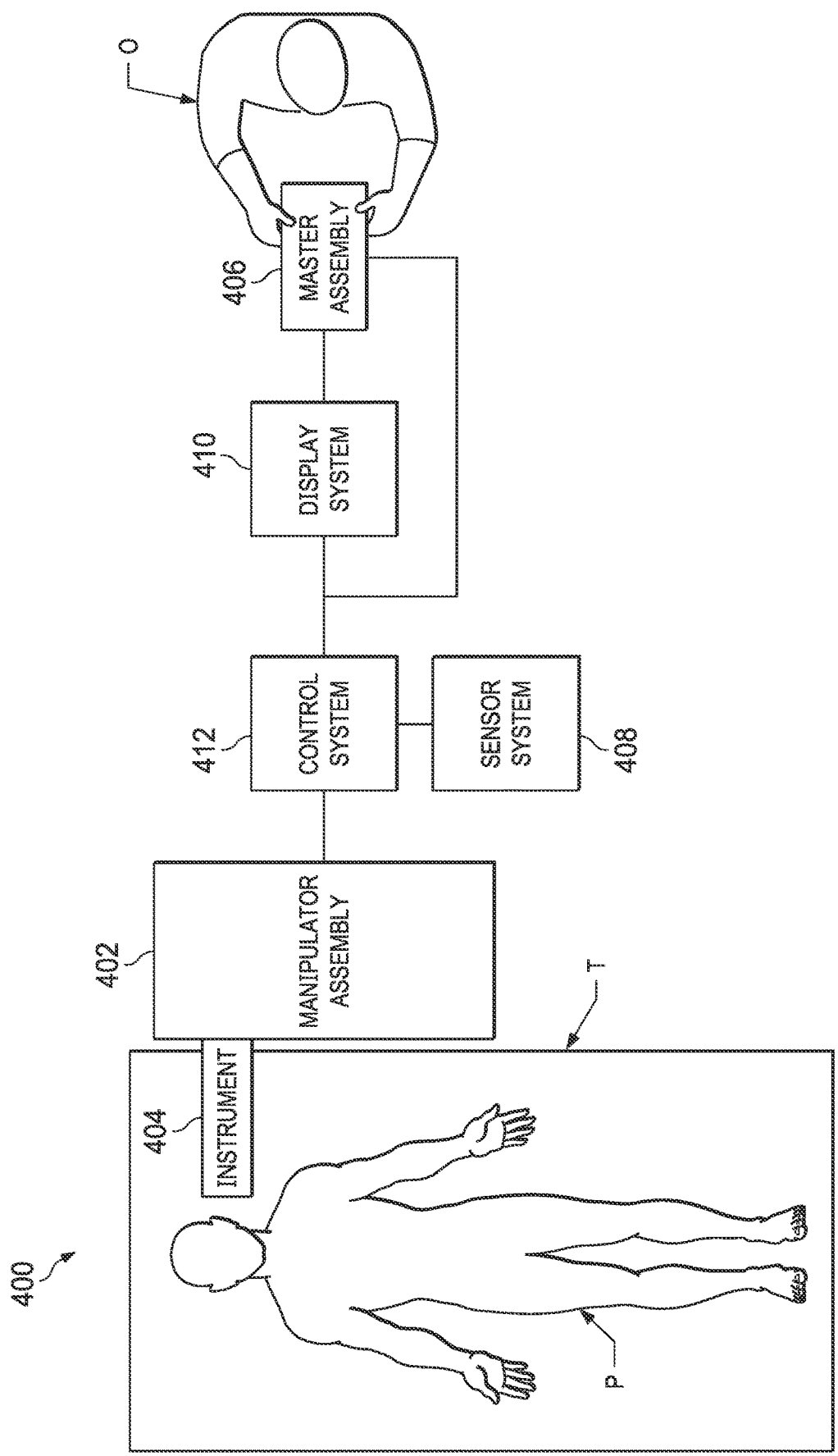
FIG. 17 is a simplified diagram of a teleoperated medical system according to some embodiments.

As shown in FIG. 17, medical system 400 generally includes a manipulator assembly 402 for operating a medical instrument 404 in performing various procedures on a patient P positioned on a table T. In some embodiments, the medical instrument 404 may include any of the antenna instruments described herein, where the antenna instruments are integrated into a distal end portion of the medical instrument 404. In alternative embodiments, the medical instrument 404 may deliver any of the antenna instruments described herein. The manipulator assembly 402 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Master assembly 406 generally includes one or more control devices for controlling manipulator assembly 402. Manipulator assembly 402 supports medical instrument 404 and may optionally include a plurality of actuators or motors that drive inputs on medical instrument 404 in response to commands from a control system 412. The actuators may optionally include drive systems that when coupled to medical instrument 404 may advance medical instrument 404 into a naturally or surgically created anatomic orifice. Other drive systems may move the distal end of medical instrument 04 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 404 for grasping tissue in the jaws of a biopsy device and/or the like. Actuator position sensors such as resolvers, encoders, potentiometers, and other mechanisms may provide sensor data to medical system 400 describing the rotation and orientation of the motor shafts. This position sensor data may be used to determine motion of the objects manipulated by the actuators.

Teleoperated medical system 400 also includes a display system 410 for displaying an image or representation of the surgical site and medical instrument 404 generated by subsystems of sensor system 408 and/or any auxiliary information related to a procedure including information related to ablation (e.g., temperature, impedance, energy delivery power levels, frequency, current, energy delivery duration, indicators of tissue ablation, etc.). Display system 410 and master assembly 406 may be oriented so operator O can control medical instrument 404 and master assembly 406 with the perception of telepresence.

In some embodiments, medical instrument 404 may include components of an imaging system, which may include an imaging scope assembly or imaging instrument that records a concurrent or real-time image of a surgical site and provides the image to the operator or operator O through one or more displays of medical system 400, such as one or more displays of display system 410. The concurrent image may be, for example, a two or three-dimensional image captured by an imaging instrument positioned within the surgical site. In some embodiments, the imaging system includes endoscopic imaging instrument components that may be integrally or removably coupled to medical instrument 404. However, in some embodiments, a separate endoscope, attached to a separate manipulator assembly may be used with medical instrument 404 to image the surgical site. In some embodiments, the imaging system includes a channel (not shown) that may provide for a delivery of instruments, devices, catheters, and/or antenna instruments described herein. The imaging system may be implemented as hardware, firmware, software or a combination thereof which interact with or are otherwise executed by one or more computer processors, which may include the processors of the control system 412.

Teleoperated medical system 400 may also include control system 412. Control system 412 includes at least one memory and at least one computer processor (not shown) for effecting control between medical instrument 404, master assembly 406, sensor system 408, and display system 410. Control system 412 also includes programmed instructions (e.g., a non-transitory machine-readable medium storing the instructions) to implement some or all of the methods described in accordance with aspects disclosed herein, including instructions for providing information to display system 410.

Control system 412 may optionally further include a virtual visualization system to provide navigation assistance to operator O when controlling medical instrument 404 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (Mt), fluoroscopy-, thermography, ultrasound, optical coherence tomography (OCT), thermal imaging, impedance imaging, laser imaging, nanotube X-ray imaging, and/or the like.

Figures 18A, 18B:
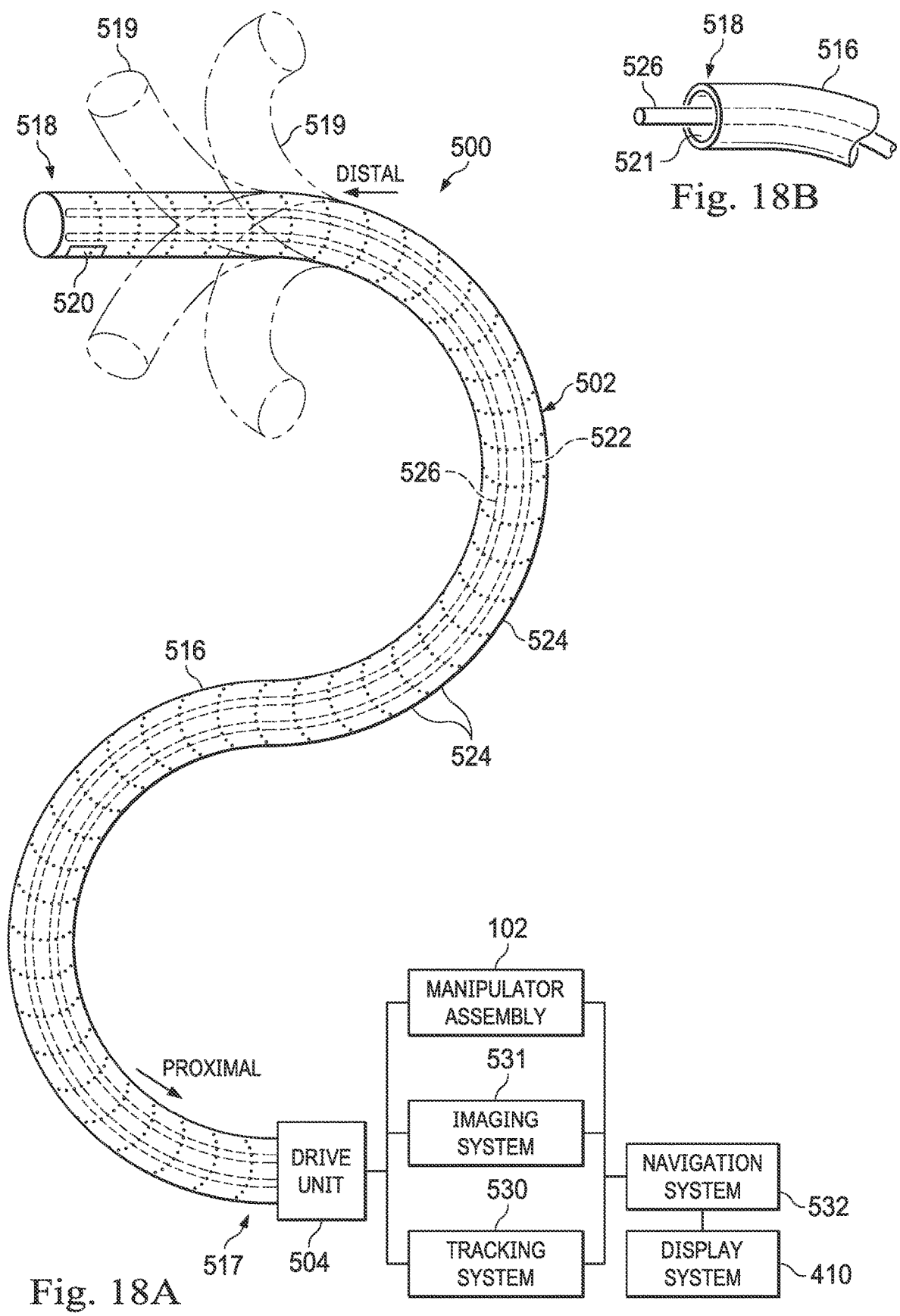
FIG. 18A is a simplified diagram of a medical instrument system according to some embodiments.
FIG. 18B is a simplified diagram of a medical instrument with an extended medical tool according to some embodiments.

FIG. 18A is a simplified diagram of a medical instrument system 500 according to some embodiments. Medical instrument system 500 includes elongate device 502, such as a flexible catheter, coupled to a drive unit 504. Elongate device 502 includes a flexible body 516 having proximal end 517 and distal end or tip portion 518. The distal end 518 may include any of the antenna instruments described herein. Medical instrument system 500 further includes a tracking system 530 for determining the position, orientation, speed, velocity, pose, and/or shape of distal end 518 and/or of one or more segments 524 along flexible body 516 using one or more sensors and/or imaging devices as described in further detail below.

Tracking system 530 may optionally track distal end 518 and/or one or more of the segments 524 using a shape sensor 522. Shape sensor 522 may optionally include an optical fiber aligned with flexible body 516 (e.g., provided within an interior channel (not shown) or mounted externally). The optical fiber of shape sensor 522 forms a fiber optic bend sensor for determining the shape of flexible body 516. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. In some embodiments, tracking system 530 may optionally and/or additionally track distal end 518 using a position sensor system 520. Position sensor system 520 may be a component of an EM sensor system with position sensor system 520 including one or more conductive coils that may be subjected to an externally generated electromagnetic field. In some embodiments, position sensor system 520 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety. In some embodiments, an optical fiber sensor may be used to measure temperature or force. In some embodiments, a temperature sensor, a force sensor, an impedence sensor, or other types of sensors may be in included within the flexible body.

Flexible body 516 includes a channel 521 sized and shaped to receive a medical instrument 526. In various embodiments, any of the antenna instruments and sheaths described above may be inserted through the channel 521 of the flexible body 516. FIG. 18B is a simplified diagram of flexible body 516 with medical instrument 526 extended according to some embodiments. In some embodiments, medical instrument 526 may be used for procedures such as imaging, visualization, surgery, biopsy, ablation, illumination, irrigation, or suction. Medical instrument 526 can be deployed through channel 521 of flexible body 516 and used at a target location within the anatomy. Medical instrument 526 may include, for example, image capture probes, biopsy instruments, laser ablation fibers, and/or other surgical, diagnostic, or therapeutic tools. Medical instrument 526 may be used with an imaging instrument (e.g., an image capture probe) also within flexible body 516. The imaging instrument may include a cable coupled to the camera for transmitting the captured image data. In some examples, the imaging instrument may be a fiber-optic bundle, such as a fiberscope, that couples to image processing system 531. The imaging instrument may be single or multi-spectral, for example capturing image data in one or more of the visible, infrared, and/or ultraviolet spectrums. Medical instrument 526 may be advanced from the opening of channel 521 to perform the procedure and then retracted back into the channel when the procedure is complete. Medical instrument 526 may be removed from proximal end 517 of flexible body 516 or from another optional instrument port (not shown) along flexible body 516.

Flexible body 516 may also house cables, linkages, or other steering controls (not shown) that extend between drive unit 504 and distal end 518 to controllably bend distal end 518 as shown, for example, by broken dashed line depictions 519 of distal end 518. In some examples, at least four cables are used to provide independent "up-down" steering to control a pitch of distal end 518 and "left-right" steering to control a yaw of distal end 518. Steerable elongate devices are described in detail in U.S. patent application Ser. No. 13/274,208 (filed Oct. 14, 2011) (disclosing "Catheter with Removable Vision Probe"), which is incorporated by reference herein in its entirety.

The information from tracking system 530 may be sent to a navigation system 532 where it is combined with information from image processing system 531 and/or the pre-operatively obtained models to provide the operator with real-time position information. In some examples, the real-time position information may be displayed on display system 410 of FIG. 17 for use in the control of medical instrument system 500. In some examples, control system 412 of FIG. 17 may utilize the position information as feedback for positioning medical instrument system 500. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 500 may be teleoperated within medical system 400 of FIG. 17. In some embodiments, manipulator assembly 402 of FIG. 17 may be replaced by direct operator control. In some examples, the direct operator control may include various handles and operator interfaces for hand-held operation of the instrument.

One or more elements in embodiments of this disclosure may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one embodiment, the control system supports wireless communication protocols such as Bluetooth, IrDA, HomeRF, IEEE 802.11, DECT, and Wireless Telemetry.

Medical tools that may be delivered through the flexible elongate devices or catheters disclosed herein may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electro-surgical electrodes, transducers, sensors, and/or the like. Medical tools may include image capture probes that include a stereoscopic or monoscopic camera for capturing images (including video images). Medical tools may additionally house cables, linkages, or other actuation controls (not shown) that extend between its proximal and distal ends to controllably bend the distal end of an antenna instrument such as elongate energy transmission member 102. Steerable instruments are described in detail in U.S. Pat. No. 7,416,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The systems described herein may be suited for navigation and treatment of anatomic tissues, via natural or surgically created connected passageway's, in any of a variety of anatomic systems, including the lung, colon, stomach, the intestines, the kidneys and kidney calices, bladder, liver, gall bladder, pancreas, spleen, the ureter, ovaries, uterus, the brain, the heart, the circulatory system including vasculature, and/or the like.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. An antenna system for tissue ablation, the antenna system comprising:
an energy transmission member;
an antenna body coupled to the energy transmission member;
a fluid source; and
a choke member including a choke body and a choke connector electrically coupling the choke body to the energy transmission member, the choke connector in direct contact with fluid from the fluid source and forming a delivery path for the fluid between the choke body and the energy transmission member, wherein the choke connector comprises a plurality of conductive beads extending between the energy transmission member and the choke body, wherein each conductive bead of the plurality of conductive beads is coupled to the choke body independent of each other conductive bead of the plurality of conductive beads.

2. The antenna system of claim 1 wherein the choke body is concentric with the energy transmission member.

3. The antenna system of claim 1 wherein the choke body is a tubular member.

4. The antenna system of claim 1 wherein the choke connector is concentric with the energy transmission member.

5. The antenna system of claim 1 wherein the plurality of conductive beads are arranged in a helical pattern.

6. The antenna system of claim 1 wherein the plurality of conductive beads are coupled to a flexible sheet that is coupled to the energy transmission member.

7. The antenna system of claim 1 further comprising:
a flexible tube extending over the energy transmission member and the choke member, wherein the delivery path for the fluid is between the flexible tube and the energy transmission member; and
a sheath extending over the flexible tube, the sheath forming a return path for the fluid dispensed from a distal end of the flexible tube.

8. An antenna system for tissue ablation, the antenna system comprising:
an energy transmission member;
an antenna body coupled to the energy transmission member;
a fluid source; and
a choke member including a choke body and a choke connector electrically coupling the choke body to the energy transmission member, the choke connector in direct contact with fluid from the fluid source and forming a delivery path for the fluid between the choke body and the energy transmission member, wherein the choke connector includes a plurality of curved projections arranged around the energy transmission member, wherein each curved projection of the plurality of curved projections is coupled to the choke body independent of each other curved projection of the plurality of curved projections.

9. The antenna system of claim 8 wherein at least one of the plurality of curved projections has a first dimension along a longitudinal axis of the energy transmission member and a second dimension perpendicular to the longitudinal axis of the energy transmission member and wherein the second dimension is greater than the first dimension.

10. The antenna system of claim 8 wherein at least one of the plurality of the curved projections extends less than 360 degrees around the energy transmission member.

11. The antenna system of claim 8 wherein the choke body is concentric with the energy transmission member.

12. The antenna system of claim 11 wherein the choke body is a tubular member.

13. The antenna system of claim 8 further comprising:
a flexible tube extending over the energy transmission member and the choke member, wherein the delivery path for the fluid is between the flexible tube and the energy transmission member; and
a sheath extending over the flexible tube, the sheath forming a return path for the fluid dispensed from a distal end of the flexible tube.

* * * * *